(12) United States Patent
Ågren et al.

(10) Patent No.: US 7,169,360 B2
(45) Date of Patent: Jan. 30, 2007

(54) ROTARY DRIVE IN AN INSTRUMENT FOR PROCESSING MICROSCALE LIQUID SAMPLE VOLUMES

(75) Inventors: Tomas Ågren, Uppsala (SE); Henrik Östlin, Uppsala (SE)

(73) Assignee: Gyros AB, Uppsala (SE)

( * ) Notice: Subject to any disclaimer, the term of this patent is extended or adjusted under 35 U.S.C. 154(b) by 676 days.

(21) Appl. No.: 10/244,667

(22) Filed: Sep. 17, 2002

(65) Prior Publication Data

US 2003/0064004 A1 Apr. 3, 2003

(30) Foreign Application Priority Data

Sep. 17, 2001 (SE) .................................... 0103108

(51) Int. Cl.
*G01N 9/30* (2006.01)
(52) U.S. Cl. .................. 422/72; 360/99.08; 360/99.12; 369/270.1; 369/271.1; 436/45; 422/99; 422/103; 422/104; 494/10
(58) Field of Classification Search .................. 422/72, 422/99, 103, 104; 436/45; 360/97.01, 99.08–99.11, 360/99.12; 369/264, 269, 270.1, 271.1; 494/10, 494/41
See application file for complete search history.

(56) References Cited

U.S. PATENT DOCUMENTS

| 3,572,890 | A | * | 3/1971 | Adamik | 435/283.1 |
| 3,608,909 | A | * | 9/1971 | Rabinow | 369/270.1 |
| 3,706,412 | A | * | 12/1972 | Latham, Jr. | 494/7 |
| 4,065,135 | A | * | 12/1977 | Doughty | 369/271.1 |
| 4,234,195 | A | * | 11/1980 | Shibata | 369/271.1 |
| 4,367,546 | A | * | 1/1983 | Shibata | 369/271.1 |
| 4,438,510 | A | * | 3/1984 | Matsumoto | 369/271.1 |
| 4,493,072 | A | | 1/1985 | Shibata | |
| 4,499,514 | A | | 2/1985 | Yamamiya et al. | |
| 5,984,319 | A | * | 11/1999 | Collonia | 279/2.05 |
| 6,021,885 | A | * | 2/2000 | Reichenbach | 198/379 |
| 6,656,428 | B1 | * | 12/2003 | Clark et al. | 422/58 |
| 2002/0098528 | A1 | * | 7/2002 | Gordon et al. | 435/7.21 |

FOREIGN PATENT DOCUMENTS

WO WO 97/21090 A1 6/1997

\* cited by examiner

*Primary Examiner*—Jan M. Ludlow
(74) *Attorney, Agent, or Firm*—Birch, Stewart, Kolasch & Birch, LLP

(57) ABSTRACT

The invention relates to a rotary drive adapted for creating liquid flow in rotatable microfluidic discs. A rotary drive for spinning a disc shaped substrate having microfluidic structures formed therein for the flow control of microliter and/or nanoliter volumes of liquid by centrifugal force is suggested, comprising a motor with a spindle having an axis of rotation. A rotary member is connected for rotation with the spindle and driven for rotation relative to a stationary member, the rotary member being formed with a top plane having a centering guide for receiving the disc so as to force a symmetry axis of the disc into alignment with said axis of rotation. A vacuum source is connected with the stationary member and communicating with the rotary member or a part thereof rotating with the rotary member for applying sub-pressure to the disc when spinning the disc about its symmetry axis. Preferably, the rotary member is journalled for contact-free rotation relative to the stationary member.

13 Claims, 2 Drawing Sheets

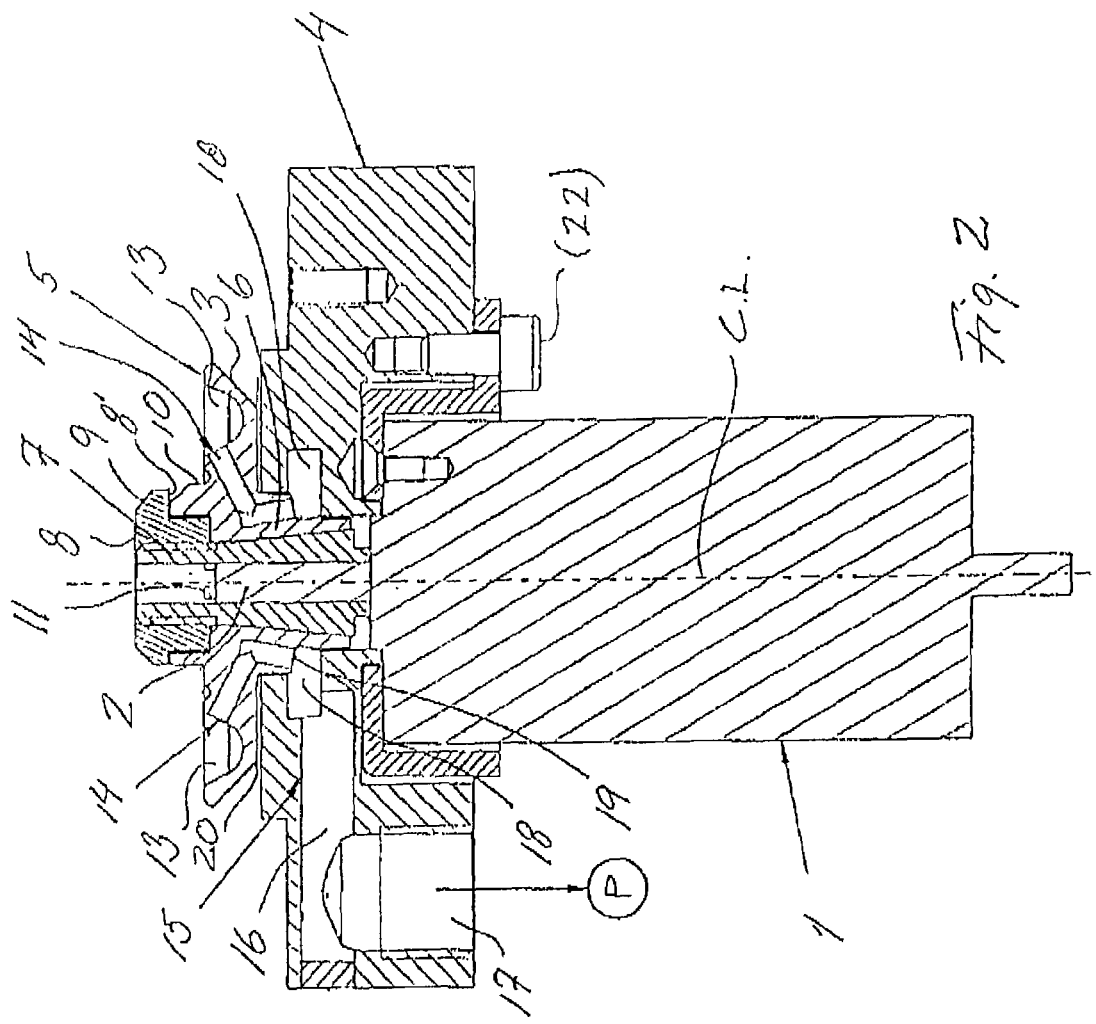
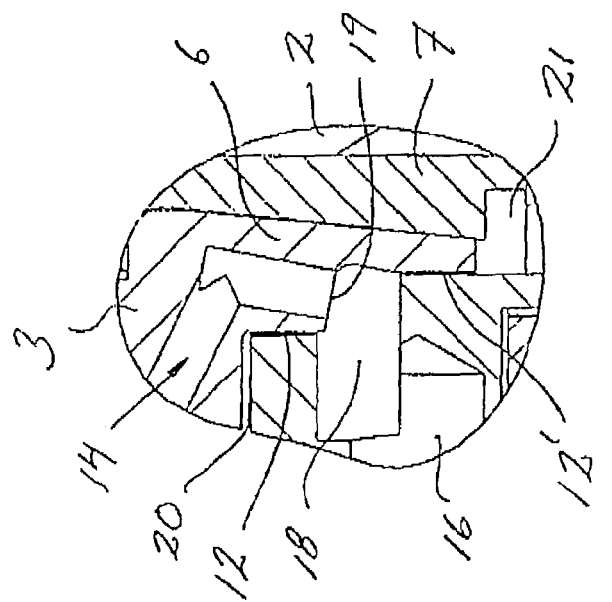

ROTARY DRIVE IN AN INSTRUMENT FOR PROCESSING MICROSCALE LIQUID SAMPLE VOLUMES

TECHNICAL FIELD

This invention relates to a rotary drive in an instrument for processing microscale liquid sample volumes, in particular for synthetic, preparative and analytic purposes, e.g. within fields such as medicine, diagnostics, biochemistry, chemistry, molecular biology, etc. More specifically, the invention relates to a rotary drive for spinning discrete liquid sample volumes that are contained in a disc shaped substrate having microfluidic structures integrally formed for the flow control of the liquid volumes by centrifugal forces in at least a part of each microfluidic structure. The rotary drive of the invention specifically serves for high seed spinning of a disc shaped substrate having micro-fluidic structures formed therein for the flow control of liquid sample volumes by centrifugal forces in a micro lab instrument for parallel processing of discrete sample volumes in the microliter and/or nanoliter range.

BACKGROUND AND PRIOR ART

The disc shaped substrate herein referred to has precisely defined microfluidic structures comprising channels, sample basins, reaction cavities, hydrophobic passages and/or other valve structures etc., by which unit operations may be integrated to perform scaled down laboratory processes. Through a high precision spinning of the disc, hundreds of analysis, for instance, may be controlled and processed in parallel on a microscale. An automated procedure may be obtained in an instrument incorporating facilities for dispensing liquid samples and reagents to the microfluidic disc, for spinning and stopping the disc in order to control the process and the movement of liquid in the microstructures, for collecting data and for moving the disc between the separate operational modules of the instrument. Preferably, the disc is disposable and molded from a synthetic material.

As used herein, the terms "microfluidic", "microstructures" etc. contemplate, that a microchannel structure comprises one or more cavities and/or channels that have a depth and/or a width that is $\leq 10^3$ μm, preferably $\leq 10^2$ μm. The lower limit for the width/breadth is typically significantly larger than the size of the largest reagents and constituents of aliquots that are to pass through a microchannel. The volumes of microcavities/microchambers are typically $\leq 1000$ nl but may extend into the μl-range such as up to 10 μl or 50 μl. Chambers/cavities directly connected to inlet ports may be considerably larger than 1000 nl, e.g. microchambers/microcavities intended for application of sample and/or washing liquids.

The terms "microscale", "microlab" contemplate, that one or more liquid aliquots introduced into a microchannel structure are in the μl-range or smaller, i.e. $\leq 1000$ μl, or in the nl-range such as $\leq 1000$ nl.

The disc comprises covered microchannel structures that are present in a substrate having an axis of symmetry. Each microchannel structure typically is oriented outwards relative to the axis of symmetry with an inlet port at a shorter radial distance from the symmetry axis than a microcavity in which a certain treatment is going to take place, for instance mixing, separation, a chemical reaction, detection etc. There may also be an outlet port for liquid downstream the reaction microcavity. Each microchannel structure may or may not be oriented in a plane perpendicular to the axis of symmetry. By spinning the disc around its axis of symmetry (axis of rotation), a liquid aliquot placed at an inner position, e.g. in an inlet port, will be subjected to a centrifugal force driving the liquid outwards, towards and through the microcavity and/or the outlet port for liquids, if present. Vent ports may also be formed and cooperating with liquid flow restrictions in the microchannel structures for controlling the flow direction of liquid aliquots inwards, towards the axis of rotation, through application of centrifugal forces.

Also other forces may be used for driving liquid flow in a certain part of the microstructures referred to, such as electrokinetic forces, capillary forces, inertia force other than centrifuged force, over-pressure, etc. It is therefore not imperative that an inlet port is at a shorter radial distance from the symmetry axis than other functional parts of a microchannel structure.

A detector arrangement with rotary drive is disclosed in a co-pending application titled "DETECTOR ARRANGEMENT WITH ROTARY DRIVE IN AN INSTRUMENT FOR PROCESSING MICROSCALE LIQUID SAMPLE VOLUMES", assigned to the same applicant and filed on the same day as the present application.

A revolving spindle is contemplated for spinning the disc, the disc being carried on a rotary member connected to the spindle. The drive means must satisfy strict demands for an accurate positioning of the disc at a halt and during spinning for sample preparation and sample dispensing, e.g., for detecting and data collection, and for high speed spinning during processing. For a time effective operation, the disc must be secured on the rotary member through a fixation that withstands considerable acceleration and retardation loads. In the process step, the disc may be hastily accelerated to speeds up to about 25,000, such as up to 10,000, revolutions per minute, or above, and hastily decelerated to a halt.

In consideration of the high rotational speeds and acceleration/deceleration loads that are involved in the process it is a technical problem to hold the disc shaped substrate on the revolving spindle, and mechanically to secure the accurate positioning of the microstructures relative to associated equipment in the microlab. Therefor, and also for reducing the accelerated mass, it is desired to avoid mechanical structures that would be subject to wear and which may also cause damage to the disc at the point of engagement.

Another technical problem related to a high speed spinning of the disc in the microlab environment is the necessity for avoiding contaminants such as minute particles down to molecular size, that might originate from frictional wear on bearings or escaping lubricants applied in a journalled connection between moving parts.

In aspects of frictional resistance and wear on scaling surfaces and sealing elements at higher rotational speeds, it is still another technical problem to establish a sub-pressure communication from a vacuum source to a rotary member on which the disc shaped substrate is seated by means of sub-pressure.

A rotary drive using sub-pressure for holding a recording medium to a revolving turntable is known from U.S. Pat. No. 4,493,072, e.g. A sub-pressure communication between the revolving turntable and a vacuum source is frictionally sealed in a stationary, bearing member, relying on lubricant grease for reducing frictional wear.

SUMMARY OF THE INVENTION

It is therefore an object of the present invention to provide a rotary drive for spinning a disc shaped substrate having microfluidic structures integrally formed for the flow control of microliter and/or nanoliter volumes of liquid by centrifugal force in an instrument for processing of microscale liquid sample volumes.

It is another object of the present invention to provide a rotary drive wherein sub-pressure is applied for holding a spinning, disc shaped substrate having microfluidic structures integrally formed for the flow control of microliter and/or nanoliter volumes of liquid by centrifugal force.

It is yet another object of the present invention to provide a rotary drive wherein a spinning, disc shaped substrate having microfluidic structures is carried for rotation on a rotary member in contact-free rotation relative to a stationary member.

It is still a further object of the present invention to provide a rotary drive for spinning a disc shaped substrate having microfluidic structures, wherein a sub-pressure communication is established from a vacuum source to a rotary member in contact-free rotation relative to a stationary member.

These and other objects are met in a rotary drive as defined in the attached claims. Briefly, a rotary drive for spinning a disc having microfluidic structures formed therein for the flow control of microliter and/or nanoliter volumes of liquid by centrifugal forces is suggested, comprising a motor with a spindle having an axis of rotation. A rotary member is non-rotationally connected with the spindle and driven for rotation relative to a stationary member, the rotary member being formed with a top plane having a centering guide for receiving the disc so as to force a symmetry axis of the disc into alignment with said axis of rotation. A vacuum source is connected with the stationary member and communicating with the rotary member for applying sub-pressure to the disc when spinning the disc about its symmetry axis.

Advantageously, the rotary member is journalled for contact-free rotation relative to the stationary member. Preferably, sub-pressure is communicated via a non-sealed sub-pressure connection that is formed in the surfaces of the rotary and stationary members and open to ambient atmosphere. These and other advantageous features are more fully described below and successively defined in the subordinated claims.

The term "rotary member" in the context of the non-sealed sub-pressure connection includes any part of the device mounted on and rotating with the spindle, including the spindle itself.

The non-sealed sub-pressure connection typically means that there is a gap providing communication with ambient air between the stationary member and the rotary member around the connection. The width of the gap complies with the rules set forth for the variants illustrated in FIGS. 3 and 4.

The rotary member typically has a flat surface perpendicular to the axis of rotation. On the flat surface there are depressions or elevations that together with a microfluidic disc that is positioned over and in contact with the surface define an enclosed sub-pressure space communicating with the vacuum source via the sub-pressure connection.

BRIEF DESCRIPTION OF DRAWINGS

The invention is further disclosed below, reference being made to the accompanying drawings showing two embodiments of the rotary drive. In the drawings.

FIG. 2 is a longitudinal section view showing the structural layout of a preferred embodiment of the rotary drive;

FIG. 3 is a partial view showing details from the structure of FIG. 1 on a larger scale.

Features that are described in the context of the embodiments of the drawings are where appropriate applicable also to the general innovative embodiment as well as to various other embodiments of the invention.

DETAILED DESCRIPTION OF THE INVENTION

Figure 1:
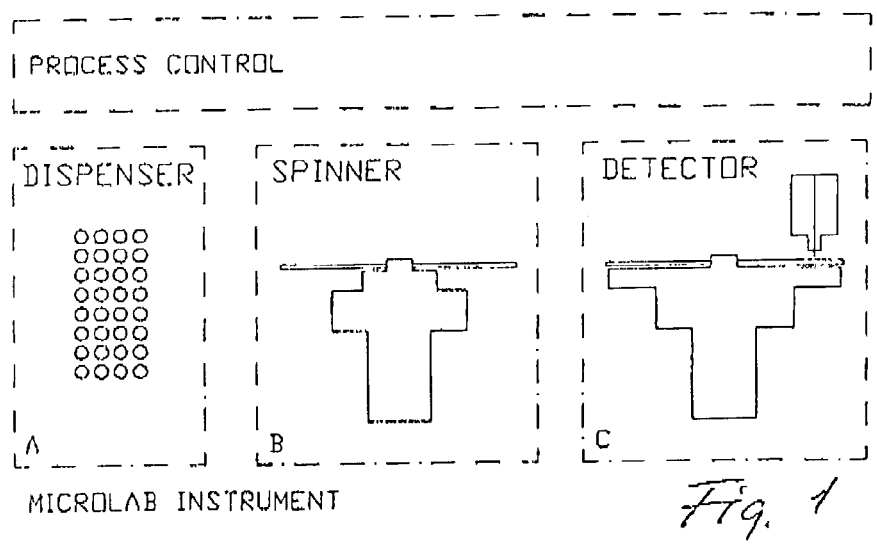
FIG. 1 is a diagrammatic view showing the set up of an instrument for processing of discrete liquid sample volumes in the microliter or nanoliter range.

An instrument for processing of discrete liquid sample volumes in the microliter or nanoliter scale, as previously discussed, is diagrammatically shown in FIG. 1 to incorporate a sample dispensing station A, a processing station B and a detecting station C. The microlab instrument preferably comprises process control means and mechanics for automated processing of discrete sample volumes in the micro- and/or nanoliter range. The term processing in this context includes liquid transport, measuring, detection, biological and/or chemical reactions, separations, for instance.

The discrete liquid sample volumes are contained in a disc shaped substrate having microfluidic structures integrally formed for the flow control of microliter and/or nanoliter volumes of liquid by centrifugal force, as previously discussed. The discs are preferably manufactured from plastic material, e.g. by replication techniques, such as embossing, molding, etc. See for instance WO 9116966 (Pharmacia Biotech AB, Öhman & Ekstroöm).

In the microstructure design, unit operations may be integrated to perform sealed down laboratory processes on a disposable disc shaped substrate. Through a compact layout of the microstructures and a high precision spinning of the disc, hundreds of analysis, for instance, may be controlled and processed in parallel on a microscale.

In operation, as previously discussed, the disc may be hastily accelerated to speeds up to about 25,000, such as up to 10,000, revolutions per minute, or above, and hastily decelerated to a halt. In the following there will be described a rotary drive for spinning the microfluidic disc while performing one or more of the processes mentioned above.

With reference to FIG. 2, a motor 1 has a spindle 2 for spinning a rotary member 3 relative to a stationary member 4. Stationary member 4 is non-rotationally connected with the motor 1. Rotary member 3 is formed with a top plane 5 for receiving the disc (not shown in the drawings) in sealing contact with the rotary member as is further described below.

The rotary member 3 has a central hub portion 6 depending from the lower side, and is non-rotationally secured to the spindle 2 by frictionally engaging a tapered sleeve 7 that is caused to be clamped about the spindle upon tightening of a nut 8 in threaded engagement with a cylindrical end portion of the tapered sleeve 7. The nut 8 has a radial flange 9 that engages a center guide 10 of the rotary member 3 and, when tightened, urges the rotary member into frictional engagement with the tapered sleeve. The sleeve 7 is radially contracting through longitudinal slots 11 that reach from the lowermost end of the sleeve to terminate above the outer end of spindle 2 in a clamped position about the spindle.

With reference also to FIG. 3, the hub portion 6 has a tapering inner wall frictionally engaging the tapered outer wall of the sleeve 7 in the clamped position. The outer periphery of the hub portion 6 is formed with a rotationally symmetric surface, mating with the inner periphery of stationary member 4. The mating surfaces of rotary member 3 and stationary member 4 are arranged with an intermediate gap 12,12' having an axial main orientation concentric about a common axis of rotation CL. In FIG. 2, the gap is diagrammatically illustrated by heavy, continuous lines 12,12' for visibility. The gap 12,12' thus defined by the mating surfaces of rotary member 3 and stationary member 4 is carefully dimensioned to operate similar to a restrictor valve for a leak flow of ambient air into a sub-pressure connection, as will be described in the following.

Returning to FIG. 2, the top plane of rotary member 3 is formed with an annular recess 13 that opens in the planar surface of top plane 5. Channels 14 are formed on the rotary member and mouthing in the annular recess 13. Alternatively, the recess 13 may be omitted and the channels 14 opening directly in the top planes 5 of rotary member 3. The channels 14 are connected to a vacuum source p for seating the disc shaped substrate on the rotary member through sub-pressure supplied from the vacuum source. The channels 14 communicate with the vacuum source via a channel 15 that is formed on the stationary member 4. The channels 14 and 15 communicate across the mating surfaces defining the gap 12,12', the gap having a radial width such that a fall of pressure will result in an air flow that is allowed to leak into the sub-pressure communication between the mating surfaces of the rotary member 3 and stationary member 4 in relative, contact-free rotation about a common axis of rotation.

In the embodiment of FIGS. 2 and 3, the mating surfaces and gaps 12,12' are annular and run concentric about the center axis CL. The channel 15 communicates with an air duct 16 that is connectable to the vacuum source p via a connection 17. The inner end of air duct 16 opens into an annular groove 18 that is formed near the longitudinal center of the mating surface of stationary member 4. Likewise, the channels 14 communicate with an annular shoulder 19 that is formed near the longitudinal center of the mating surface of rotary member 3. The annular groove 18 and the mouths of channels 14 in the shoulder 19 define a sub-pressure connection that crosses the gap 12,12' and separates an axially outer portion 12 from an axially inner portion 12' of the gap. The axial lengths of the outer and inner portions of gap 12,12' are shown to be substantially the same, however this is not crucial for the operation of the contact-free and seal free sub-pressure connection.

The gap 12,12' is longitudinally open to ambient atmosphere in both axial directions of the gap. The axially upper portion 12 opens into a radial space 20 that separates the rotary member axially from the stationary member. The axially inner portion 12' opens into an annular space 21 that is ventilated through the center of sleeve 7, via the slots 11. The ventilation ensures that the rotary member is axially balanced relative to the stationary member, and avoids an exaggerated axial load on spindle bearings (not shown) in the motor 1.

The mating surfaces of rotary member 3 and stationary member 4 are machined within small tolerances to provide a gap 12,12' having a width in the range of a few hundredths of a millimeter, i.e. a gap width of approximately 0.001 to 0.90 mm, such as 5–40 µm. The width of gap 12,12' is related to the overall diameter of the gap, the actual capacity of the vacuum source and the desired holding force applied to the disc, and hence the suggested gap dimension is merely an example to guide the technician.

An adjustable gap dimension may be achieved when the mating surfaces are formed with a taper and the rotary and stationary members are mutually adjustable (22) in the longitudinal direction of the spindle 2, thus providing a possibility for controlling the radial dimension of the gap, and thereby controlling the loss of pressure in the air that is allowed to leak into the sub-pressure connection 18,19.

The rotary drive as disclosed above is free of friction losses, and operates with less energy consumption and motor power. Also, the angular momentum in acceleration is lower, which spares the motor and spindle bearings.

Figure 4:
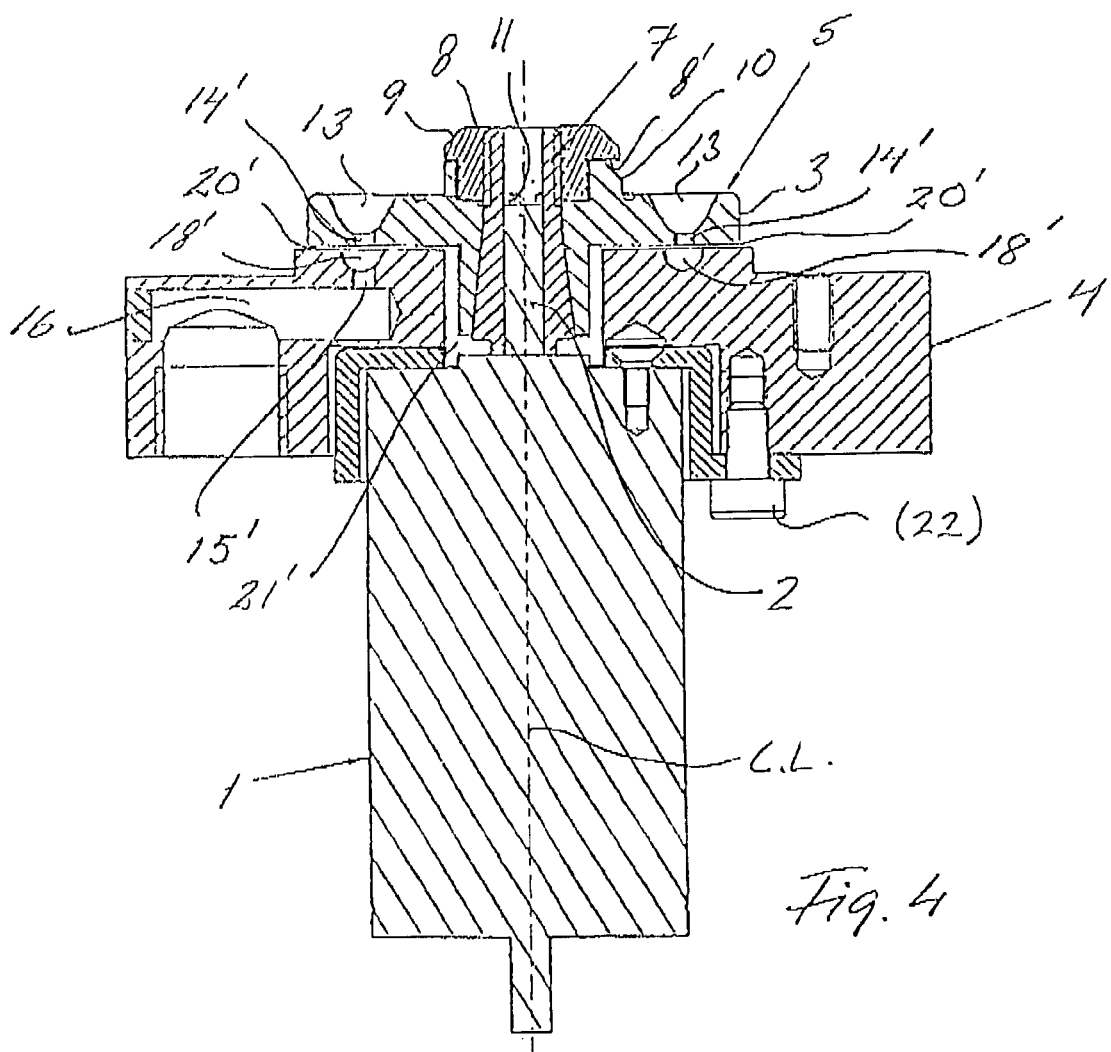
FIG. 4 illustrates an alternative embodiment of the rotary drive in a view corresponding with FIG. 2.

An alternative embodiment is illustrated in FIG. 4, wherein corresponding details are identified by the same reference numerals that are used in FIGS. 2 and 3. The modified rotary drive of FIG. 4 contemplates that a gap 20' has an axial width and extends in a radial main orientation about the axis of rotation CL. In this embodiment, channels 14' open in the top plane and the bottom surface, respectively, of rotary member 3. An annular groove 18' in a top surface of the stationary member 4 communicates with air duct 16 through a channel 15'. An adjustable gap dimension may be achieved when the rotary and stationary members are mutually adjustable (22) in the longitudinal direction of the spindle 2, thus providing a possibility for controlling the width of the gap 20', and thereby controlling the loss of pressure in the air that is allowed to leak into the sub-pressure connection 14',18'. Adjustment may be achieved by means of a set screw 22, or by insertion of shims (not shown in the drawings), e.g. The radially outer periphery of the gap 20' opens circumferentially of the rotary member 3, and the radially inner periphery of gap 20' opens into an annular space 21' that is ventilated through the center of sleeve 7, via the slots 11.

In all embodiments, an adjustable gap width may also be achieved by providing a reversibly expandable ring, e.g. a piezoelectric ring (not shown in the drawings) on the stationary member 4. Advantageously, a ceramic ring with piezoelectric properties is received on the stationary member and electrically supplied via an adjustable voltage control. The piezoelectric ring may be recessed to flush with the surface facing the gap 12,12',20', concentric about the axis of rotation, and where appropriate on both sides of a sub-pressure connection that communicates with the gap. By controlling the voltage applied to the piezoelectric ring, the loss of pressure over the gap may be controlled by expanding/contracting the ring to adjust the gap width. Depending on the material in the ring, means other than voltage control may be used for controlling expansion/contraction of the ring and thereby also the loss of pressure over the gap.

The center guide 10 is dimensioned to receive the disc shaped substrate, the disc having a central through hole dimensioned to be frictionally engaging the periphery of the center guide 10 when the disc is seated on the rotary member. Alternatively, or in combination therewith, the center guide 10 may be formed with a protrusion for arresting the disc on the rotary member. Preferably, the periphery of the center guide 10 is beveled for partially engaging the inner periphery of the disc at angularly and equally spaced portions thereof. Advantageously, the nut 8 is oval in shape or otherwise formed with an overhung portion 8' that will catch the disc in case of a vacuum failure.

A pressure driven vacuum ejector may be used for supplying sub-pressure to the disc. Advantageously, the ejector may also be controlled to provide an air blow through the sub-pressure communication, for pushing the disc out of engagement with the center guide or for lifting the disc from the top plane, if needed.

Modifications are possible without departing from the teachings advised herein. The appended claims should however be construed to incorporate any and all of such modifications to the invention, that will become apparent for the man of ordinary skill in this art when studying the disclosure given herein.

The invention claimed is:

1. A rotary drive for spinning a disc about a symmetry axis thereof, the rotary drive comprising:
   a motor and a spindle, the spindle having an axis of rotation;
   a stationary member;
   a rotary member supported for rotation with the spindle, the rotary member being formed with a top plane having a centering guide for receiving the disc so as to force the symmetry axis of the disc into alignment with said axis of rotation, wherein the motor is operative for driving the rotary member for contact-free rotation relative to the stationary member; and
   a vacuum source connected with the stationary member and communicating with the rotary member or a part rotating with the rotary member for applying sub-pressure to the disc in order to hold the disc on the rotary member when spinning the disc about its symmetry axis,
   wherein there is a sub-pressure connection for providing sub-pressure to the rotary member defined by mutually mating surfaces of the rotary and the stationary member, respectively, that are in contact-free rotation relative to each other.

2. The rotary drive of claim 1, wherein the rotary member is formed with a hub portion concentric about the spindle and reaching through a center of the stationary member, and a sub-pressure connection being formed in an outer surface of said hub portion and in an inner surface of the stationary member which inner surface mates with said outer surface.

3. The rotary drive of claim 1, wherein the centering guide has a radial projection for arresting the disc on the rotary member.

4. The rotary drive of claim 1, wherein the rotary member carries a disc having microfluidic structures which are adapted for flow control of microliter and/or nanoliter volumes of liquid by centrifugal force created by rotating the rotary member about said axis of rotation.

5. The rotary drive of claim 1, wherein the mutually mating surfaces of the rotary and stationary members in contact-free relative rotation are spaced to define a gap that provides leakage of ambient air into the sub-pressure connection.

6. The rotary drive of claim 5, wherein the spacing between the mating surfaces of the rotary and stationary members is dimensioned to provide a loss of pressure in the air, leaking into the sub-pressure connection.

7. The rotary drive of claim 5, wherein the width of said gap between the rotary member and the stationary member is adjustable.

8. The rotary drive of claim 5, wherein the width of said gap is adjustable by means of a set screw controlling the axial distance between the rotary member and the stationary member.

9. The rotary drive of claim 5, wherein the width of said gap between the rotary member and the stationary member is adjustable by means of a piezoelectric ring supported on the stationary member and/or the rotary member, and facing the gap.

10. The rotary drive of claim 5, wherein said gap has a radial main orientation about the axis of rotation.

11. The rotary drive of claim 5, wherein said gap has an axial main orientation about the axis of rotation.

12. The rotary drive of claim 5, wherein the gap is concentric about the axis of rotation and opens to ambient air longitudinally in both axial directions, for axially balancing the rotary member relative to the stationary member.

13. The rotary drive of claim 5, wherein the gap is tapered and controllable by axially adjusting the relative position of the rotary and stationary members.

* * * * *